(12) United States Patent
Murayama et al.

(10) Patent No.: US 11,921,082 B2
(45) Date of Patent: Mar. 5, 2024

(54) MEASURING DEVICE

(71) Applicant: YOKOGAWA ELECTRIC CORPORATION, Musashino (JP)

(72) Inventors: Kodai Murayama, Musashino (JP); Yoshiaki Tanaka, Musashino (JP); Kenji Oishi, Musashino (JP); Masahiro Hirase, Musashino (JP); Yuzuho Iga, Musashino (JP)

(73) Assignee: YOKOGAWA ELECTRIC CORPORATION, Musashino (JP)

( * ) Notice: Subject to any disclaimer, the term of this patent is extended or adjusted under 35 U.S.C. 154(b) by 346 days.

(21) Appl. No.: 17/279,747

(22) PCT Filed: Sep. 4, 2019

(86) PCT No.: PCT/JP2019/034860
§ 371 (c)(1),
(2) Date: Mar. 25, 2021

(87) PCT Pub. No.: WO2020/066518
PCT Pub. Date: Apr. 2, 2020

(65) Prior Publication Data
US 2022/0050077 A1 Feb. 17, 2022

(30) Foreign Application Priority Data
Sep. 27, 2018 (JP) .................. 2018-182466

(51) Int. Cl.
G01N 27/403 (2006.01)
A61B 5/1486 (2006.01)
(Continued)

(52) U.S. Cl.
CPC ....... G01N 27/4148 (2013.01); A61B 5/1486 (2013.01); G01N 27/301 (2013.01); G01N 27/36 (2013.01); G01N 27/4167 (2013.01)

(58) Field of Classification Search
CPC ............ G01N 27/4148; G01N 27/301; G01N 27/302; G01N 27/36; G01N 27/4167;
(Continued)

(56) References Cited

U.S. PATENT DOCUMENTS

| 7,086,288 B2 * | 8/2006 | Lee ................. G01N 33/54373 73/718 |
| 2002/0029964 A1 * | 3/2002 | Matsumoto ............ C12Q 1/002 204/403.1 |

(Continued)

FOREIGN PATENT DOCUMENTS

| JP | 2002055076 A | 2/2002 |
| JP | 2003525432 A | 8/2003 |

(Continued)

OTHER PUBLICATIONS

English translation of the Written Opinion for International application No. PCT/JP2019/034860, dated Dec. 12, 2019 (Year: 2019).*

(Continued)

Primary Examiner — Alexander S Noguerola
(74) Attorney, Agent, or Firm — KENJA IP LAW PC

(57) ABSTRACT

A measuring device 1 according to the present disclosure measures a state of a solution L. The measuring device 1 includes a measuring unit 10 that outputs a measurement signal associated with the state of the solution L, a protection unit 20 attached to the measuring unit 10, and a controller 40 that obtains the information on the state of the solution L on the basis of a measurement signal output from the measuring unit 10. The measuring unit 10 has a first part P1 in a usable state that contributes to output of the measurement signal by coming into contact with the solution L, and a second part that is isolated from the solution L by the protection unit 20 and is in a standby state for measurement.

6 Claims, 10 Drawing Sheets

(51) Int. Cl.
*G01N 27/30* (2006.01)
*G01N 27/36* (2006.01)
*G01N 27/414* (2006.01)
*G01N 27/416* (2006.01)

(58) Field of Classification Search
CPC ......... G01N 21/553; G01N 2021/5903; G01N 2021/258; A61B 5/1486
See application file for complete search history.

(56) References Cited

U.S. PATENT DOCUMENTS

| | | | |
|---|---|---|---|
| 2003/0150726 A1* | 8/2003 | West | G01N 27/36 204/435 |
| 2007/0299385 A1* | 12/2007 | Santini, Jr. | B01J 19/0093 422/417 |
| 2016/0003761 A1 | 1/2016 | Clark et al. | |
| 2016/0235347 A1 | 8/2016 | Baig et al. | |
| 2017/0160222 A1* | 6/2017 | Kohlmann | G01N 27/283 |

FOREIGN PATENT DOCUMENTS

| | | | | |
|---|---|---|---|---|
| JP | 2006275923 A | 10/2006 | | |
| JP | 2007093613 A | 4/2007 | | |
| JP | 2007512859 A | 5/2007 | | |
| JP | 2008544221 A | 12/2008 | | |
| JP | 2009236687 A | 10/2009 | | |
| JP | 2010025728 A | 2/2010 | | |
| WO | 0164344 A2 | 9/2001 | | |
| WO | 2005041767 A2 | 5/2005 | | |
| WO | 2006133171 A2 | 12/2006 | | |
| WO | WO 2012130773 A1 * | 10/2012 | | A61B 5/145 |
| WO | WO 2012130773 A2 * | 10/2012 | | A61B 5/145 |
| WO | 2012158202 A2 | 11/2012 | | |

OTHER PUBLICATIONS

Takashi Fujimaki, Current status and prospects of biodegradable polymers, Kobunshi, 1996, pp. 141-145, vol. 45, Issue 3 with a partial English translation.

* cited by examiner

MEASURING DEVICE

CROSS-REFERENCE TO RELATED APPLICATION

The present application claims priority to and benefit of Japanese Patent Application No. 2018-182466 filed on Sep. 27, 2018, the entire contents of which are incorporated herein by reference.

TECHNICAL FIELD

The present disclosure relates to a measuring device configured to measure a state of a solution.

BACKGROUND

Techniques for measuring the concentration of any ions such as hydrogen ions contained in a solution are known.

For example, Patent Literature 1 (PTL 1) discloses an Ion Sensitive Field Effect Transistor (ISFET) ion sensor that can be miniaturized and solidified with an excellent reproducibility and stability of measurement results due to an excellent stability of a reference part and an excellent chemical and physical durability.

CITATION LIST

Patent Literature

PLT 1: JP2009-236687 (A)

SUMMARY

Technical Problem

However, a portion of a measuring unit in contact with a solution deteriorates with use due to causes such as adhesion of foreign matter, alteration, scraping, etc., and an accurate measurement signal cannot be output from the measuring unit. In the case of the ion sensor described in PTL 1, for example, an ion sensitive film gradually deteriorates due to contact with a solution. In such a case, the user needs to replace the ion sensor with a new one in a short period of time, which is inconvenient.

It is therefore an object of the present disclosure to provide a measuring device that can measure a state of a solution over a long period of time and improves user convenience.

Solution to Problem

A measuring device according to some embodiments is a measuring device configured to measure a state of a solution. The measuring device includes a measuring unit configured to output a measurement signal associated with the state of the solution, a protection unit attached to the measuring unit, and a controller configured to obtain information on the state of the solution on the basis of the measurement signal output from the measuring unit. The measuring unit has a first part in a usable state that contributes to output of the measurement signal by coming into contact with the solution, and a second part that is isolated from the solution by the protection unit and is in a standby state for measurement. In this manner, the state of the solution can be measured over a long period of time and the user convenience is improved. More specifically, the measuring unit has the second part in a standby state for measurement, thus the cycle of maintenance work including calibration and refill of an inner solution is extended, which allows for a long-term measurement. For example, with the measuring device, continuous measurement on a year-to-year basis is possible.

In an embodiment, the protection unit has a protection plate that isolates the second part of the measuring unit from the solution, and the protection plate may be composed of at least one of biodegradable resin and acid-soluble resin. Thus, since the second part of the measuring unit is not in contact with the solution, deterioration of the second part of the measuring unit is suppressed. The second part of the measuring unit can remain unused while the measurement by the first part is continued. Since the protection plate is composed of at least one of biodegradable resin and acid-soluble resin, the protection plate is decomposed or dissolved by the solution even if it is detached from the measuring unit. Therefore, the protection plate can be prevented from remaining as a foreign matter in the solution.

In an embodiment, the protection unit may further include a heater that heats an attaching portion of the protection plate to the measuring unit, which enables control of the state of the attaching portion of the protection plate to the measuring unit by heating by the heater.

In an embodiment, the attaching portion may include a thermally soluble adhesive having a melting point higher than the temperature of the solution and lower than the temperature at which it is heated by the heater, and the protection plate may be attached to the measuring unit by the thermally soluble adhesive. Thus, when the thermally soluble adhesive included in the attaching portion is melted through heating by a heater, the protection plate is detached from the measuring unit. Therefore, control by the heater allows control of the second part of the measuring unit to switch from the standby state for measurement to the usable state, which makes control of switching easy.

In an embodiment, when determining that a measured value of the information on the state of the solution exceeds a predetermined range that can be measured by the first part of the measuring unit, the controller may detach the protection plate from the measuring unit through heating by the heater, and obtain the measurement signal based on the second part. In this manner, even if it is impossible to measure based on the first part of the measuring unit, it is possible to switch to measurement based on the second part of the measuring unit. Therefore, the state of the solution can be measured over a long period of time, and the user convenience is improved.

In an embodiment, an inner solution or gel with known properties may be filled between the protection plate and the second part of the measuring unit. This allows for calibration of the measuring device using the second part of the measuring unit until immediately before the controller detaches the protection plate.

In an embodiment, the information on the state of the solution may include a pH concentration, the measuring unit may have a glass electrode unit, a first reference electrode unit and a second reference electrode unit used for glass electrode type pH measurement, the first part may have a pair including the glass electrode unit and the first reference electrode unit, and the second part may have the second reference electrode unit. Thus, the cycle of maintenance work including calibration and refill of an inner solution is extended even when a conventional glass electrode type pH measuring device is used, thus a long-term measurement is possible.

In an embodiment, the distance between the internal electrode contained in the glass electrode unit and the internal electrode contained in the first reference electrode unit may be the same as that between the internal electrode contained in the glass electrode unit and the internal electrode contained in the second reference electrode unit. Therefore, the distance between the internal electrode of the glass electrode unit and the internal electrode of each reference electrode unit is constant, and thus measurement errors are reduced between the measurement results when the internal electrode of each reference electrode unit is used.

In an embodiment, the information on the state of the solution may include an ion concentration, the measuring unit may have a first ion sensitive field effect transistor and a second ion sensitive field effect transistor, the first part may have the first ion sensitive field effect transistor and the second part may have the second ion sensitive field effect transistor. Thus, even when a conventional ion sensitive field effect transistor (ISFET) type measuring device is used, the cycle of maintenance work is extended, which allows for a long-term measurement. The measuring unit composed of a small ISFET allows the measuring device 1 to be kept small.

Advantageous Effect

According to the present disclosure, a measuring device that can measure a state of a solution over a long period of time and improve user convenience can be provided.

DETAILED DESCRIPTION

An embodiment of the present disclosure will be mainly described below with reference to the accompanying drawings. In the following drawings, for the sake of simplicity of description, the illustration of predetermined components is omitted as appropriate. For example, a solution L described later is omitted in FIGS. 3, 6, 7, 9 and 10.

First Embodiment

Configurations and functions of the measuring device 1 according to the first embodiment will be mainly described with reference to FIGS. 1-8.

Figure 1:
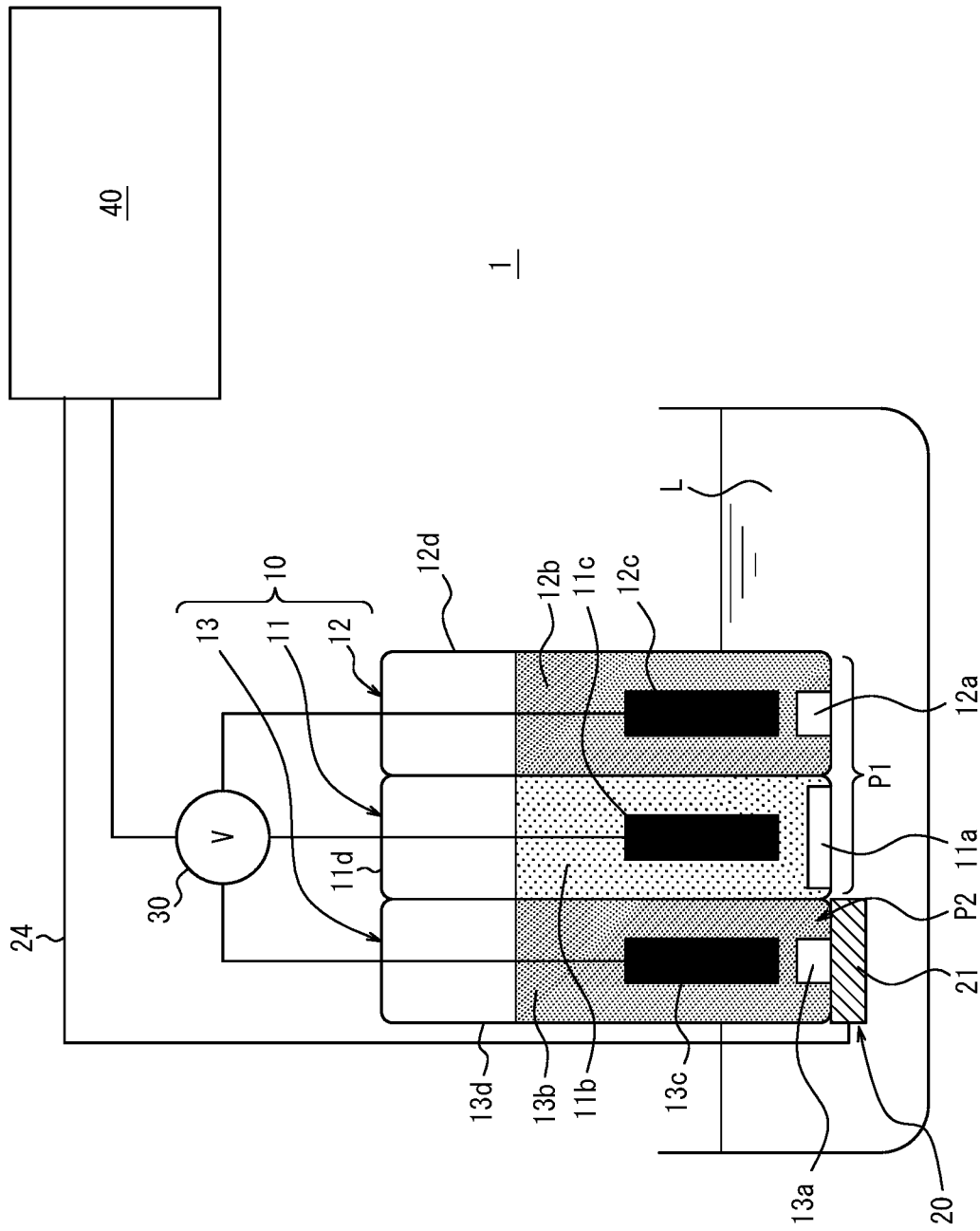
FIG. 1 is a schematic diagram illustrating an example of configuration of a measuring device according to a first embodiment.

FIG. 1 is a schematic diagram illustrating an example of configuration of the measuring device 1 according to the first embodiment. The measuring device 1 according to the first embodiment obtains the information on a state of a solution L. In the first embodiment, the "information on the state of the solution L" includes a pH concentration, i.e. a hydrogen ion concentration. The measuring device 1 according to the first embodiment has a plurality of electrode units used for the glass electrode type pH measurement. Referring to FIG. 1, the measuring device 1 has a measuring unit 10 and a protection unit 20 attached to the measuring unit 10.

The measuring unit 10 outputs a measurement signal associated with the state of the solution L. The measuring unit 10 has a first part P1 in a usable state and a second part P2 in a standby state for measurement. The "usable state" includes the state of the measuring unit 10 that can contribute to output of a measurement signal associated with the state of the solution L by coming into contact with the solution L. More specifically, in the first embodiment, the "usable state" includes the state of the measuring unit 10 that can contribute to output of a measurement signal based on the glass electrode type pH measurement. The "standby state for measurement" includes the state of the measuring unit 10 that is isolated from the solution L by the protection unit 20 and does not contribute to output of a measurement signal associated with the state of the solution L. More specifically, in the first embodiment, the "standby state for measurement" includes the state of the measuring unit 10 that does not contribute to output of a measurement signal based on the glass electrode type pH measurement.

The first part P1 of the measuring unit 10 has a pair including a glass electrode unit 11 and a first reference electrode unit 12. The glass electrode unit 11 includes a glass thin film 11a that responds to hydrogen ions, an inner solution 11b with a known pH concentration, an internal electrode 11c for reading electric signals and a support 11d that supports the internal electrode 11c. The glass thin film 11a is attached to the end of the support 11d. The inner solution 11b is filled inside the support 11d. The inner solution 11b may include any solution, such as a pH 7 phosphate buffer solution. The internal electrode 11c is immersed in the inner solution 11b filled inside the support 11d.

The first reference electrode unit 12 has a liquid junction 12a, an inner solution 12b with a known pH concentration and a small liquid junction potential, an internal electrode 12c for reading electrical signals and a support 12d that supports the internal electrode 12c. The liquid junction 12a is disposed on the end of the support 12d and has a plurality of fine holes. The inner solution 12b is filled inside the support 12d. The inner solution 12b may include any solution such as a KCL solution. The inner solution 12b diffuses into the solution L via the liquid junction 12a. The internal electrode 12c is immersed in the inner solution 12b filled inside the support 12d.

In the glass electrode type pH measurement based on the first part P1, two different kinds of solutions are disposed inside and outside the support 11d with respect to the glass thin film 11a. That is, the inner solution 11b and the solution L are disposed. At this time, an electromotive force proportional to the difference in the pH concentration between the inner solution 11b and the solution L is generated on both surfaces of the glass thin film 11a. The internal electrode 11c immersed in the inner solution 11b generates an electromotive force corresponding to the electromotive force generated on both surfaces of the glass thin film 11a. On the other hand, the internal electrode 12c immersed in the inner solution 12b always generates a constant electromotive force while being in electrical contact with the solution L as the inner solution 12b diffuses into the solution L through the liquid junction 12a.

As described above, in the first part P1 of the measuring unit 10, the inner solution 12b is diffused little by little from the liquid junction 12a to maintain the electrical connection between the internal electrode 12c of the first reference electrode unit 12 and the solution L. Therefore, the inner solution 12b gradually decreases over the measurement time as the pH concentration of the solution L is measured by the measuring device 1. When the inner solution 12b is empty, measurement using the first part P1 of the measuring unit 10 becomes impossible. Therefore, in the conventional glass electrode type pH measuring device having no second part P2 and the protection unit 20, due to the above described factors, the maintenance work including calibration and refill of the inner solution 12b occurs in a short period of time of about one to three months, for example. Although it is possible to increase the amount of inner solution 12b to extend the maintenance work cycle, in this case, the support 12d that contains the inner solution 12b will become large, and as a result, the whole glass electrode type pH measuring device becomes large. As described above, in the prior art, it is difficult to perform a long-term measurement using a glass electrode type pH measuring device while keeping the glass electrode type pH measuring device small, and the user convenience is low.

The measuring device 1 according to the first embodiment solves the above described problem, realizes measurement of the solution L over a long period of time, and improves the user convenience. Thus, the measuring device 1 has the second part P2 of the measuring unit 10 and the protection unit 20.

The second part P2 of the measuring unit 10 has a second reference electrode unit 13, which is different from a pair of the glass electrode unit 11 and the first reference electrode unit 12 in the usable state. The second reference electrode unit 13 has a liquid junction 13a, an inner solution 13b with a known pH concentration and a small liquid junction potential, an internal electrode 13c for reading electrical signals and a support 13d that supports the internal electrode 13c. The liquid junction 13a is disposed on the end of the support 13d and has a plurality of fine holes. The inner solution 13b is filled inside the support 13d. The inner solution 13b may include any solution such as a KCL solution. Diffusion of the inner solution 13b to the solution L via the liquid junction 13a is suppressed by the protection unit 20. The internal electrode 13c is immersed in the inner solution 13b filled inside the support 13d.

The distance between the internal electrode 11c contained in the glass electrode unit 11 and the internal electrode 12c contained in the first reference electrode unit 12 may be the same as that between the internal electrode 11c and the internal electrode 13c contained in the second reference electrode unit 13. In this manner, the distance between the internal electrode 11c of the glass electrode unit 11 and the internal electrode of each reference electrode unit is constant, and thus measurement errors are reduced between the measurement result when the internal electrode 11c and the internal electrode 12c are used and the measurement result when the internal electrode 11c and the internal electrode 13c are used.

Figure 2:
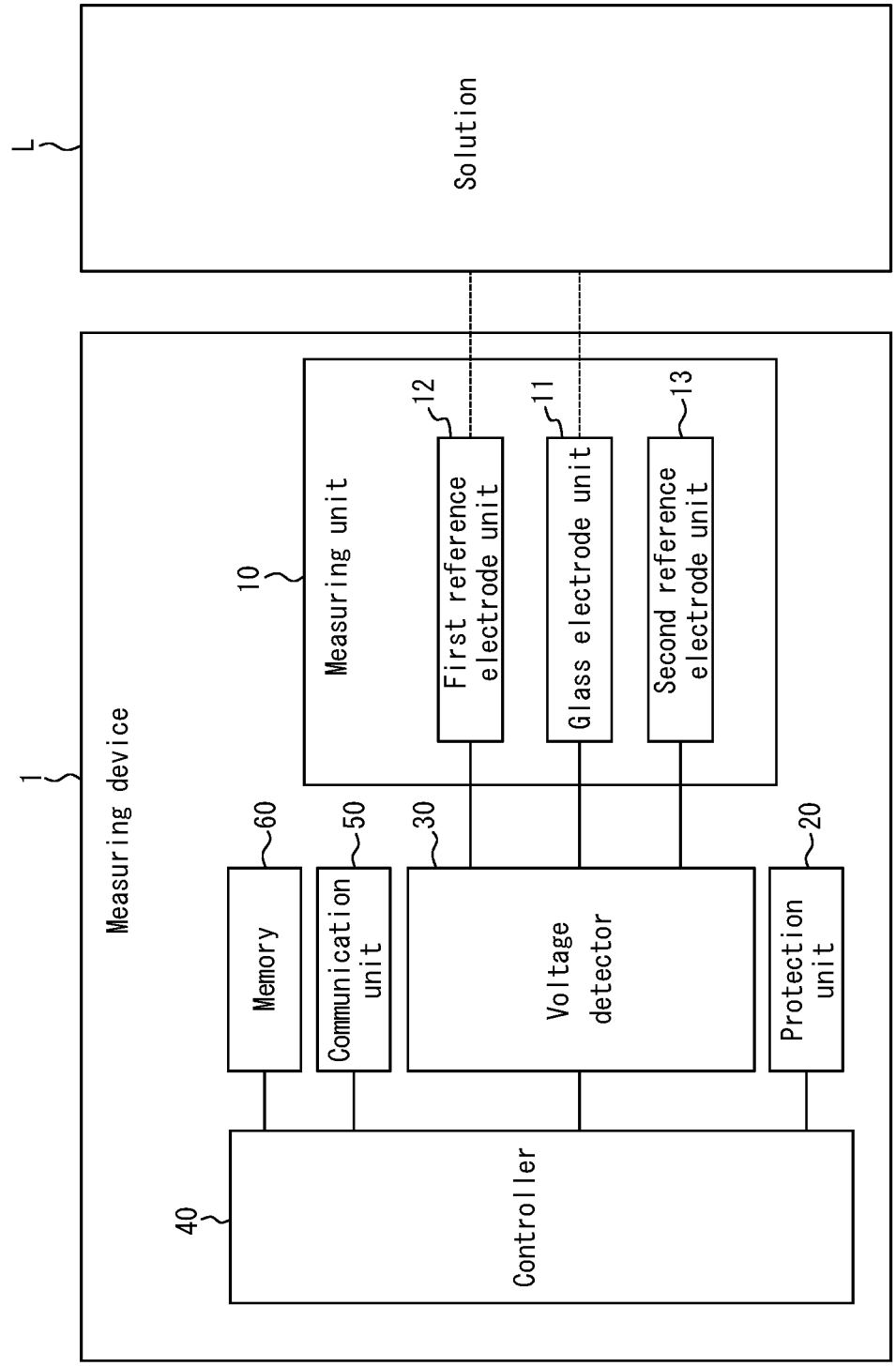
FIG. 2 is a block diagram including the measuring device in FIG. 1 and a solution.

FIG. 2 is a block diagram including the measuring device 1 and the solution L. Referring to FIG. 2, the measuring device 1 has the measuring unit 10 including the glass electrode unit 11, the first reference electrode unit 12 and the second reference electrode unit 13 and the protection unit 20. In addition, the measuring device 1 has a voltage detector 30, a controller 40, a communication unit 50 and a memory 60.

The voltage detector 30 includes any voltage sensor capable of detecting a voltage. The voltage detector 30 detects the difference in electromotive force, that is, a voltage, generated between the internal electrode 11c of the glass electrode unit 11 and the internal electrode 12c of the first reference electrode unit 12. The voltage detector 30 switches the connection with the internal electrode 12c to the connection with the internal electrode 13c of the second reference electrode unit 13 in response to switching from the measurement based on the first reference electrode unit 12 to the measurement based on the second reference electrode unit 13 described later.

The controller 40 includes one or more processors. For example, the controller 40 includes a processor that enables processing related to the measuring device 1. The controller 40 is connected to each component constituting the measuring device 1, and controls and manages the entire measuring device 1 including each component. The controller 40 obtains the information on the state of the solution L on the basis of the measurement signal output from measuring unit 10. More specifically, the controller 40 calculates the pH concentration of the solution L on the basis of the voltage signal from the measuring unit 10 obtained via the voltage detector 30.

The communication unit 50 includes any communication interface corresponding to any communication protocol based on wire or wireless. The communication unit 50 may transmit the information on the state of the solution L obtained by the controller 40 to any external device. The communication unit 50 may receive a control signal for controlling an electrode heater 23 of the protection unit 20 described later from any external device.

The memory 60 includes any memory such as Hard Disk Drive (HDD), Solid State Drive (SSD), Electrically Erasable Programmable Read-Only Memory (EEPROM), Read-Only Memory (ROM) and Random Access Memory (RAM), and stores the information required for realizing operation of the measuring device 1. The memory 60 may function as a main storage device, an auxiliary storage device, or a cache memory. The memory 60 is not limited to those built in the measuring device 1, and may be an external memory connected by a digital input/output port such as a USB. The memory 60 stores, for example, the information on the state of the solution L obtained by the controller 40.

Figure 3:
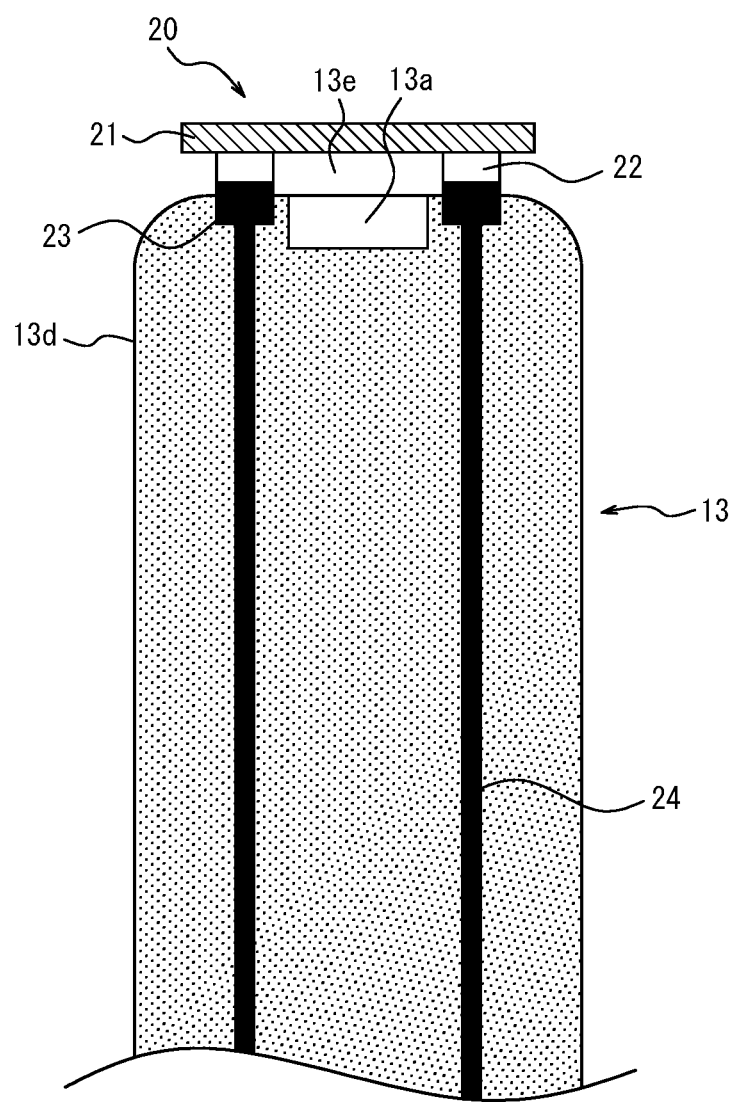
FIG. 3 is an enlarged view of an end portion of a second reference electrode unit in FIG. 2.

FIG. 3 is an enlarged view of an end portion of the second reference electrode unit 13 in FIG. 2. In FIG. 3, the inner solution 13b and the internal electrode 13c contained in the support 13d are not illustrated. Configuration and function of the protection unit 20 will be mainly described with reference to FIG. 3.

The protection unit 20 has a protection plate 21 that isolates the second part P2 of the measuring unit 10 from the solution L. More specifically, the protection plate 21 electrically isolates the second reference electrode unit 13 contained in the second part P2 from the solution L. The protection plate 21 may be composed of, for example, at least one of biodegradable resin and acid-soluble resin including resin having a controlled molecular weight of acrylic acid type, phthalic acid type and the like. Configuration of the protection plate 21 is not limited thereto. The protection plate 21 may be composed of any material having neither biodegradability nor acid solubility.

The protection plate 21 is attached, for example, to the end surface side of the support 13d of the second reference electrode unit 13 of the measuring unit 10 by adhesion with a heat-soluble adhesive 22. The heat-soluble adhesive 22 is any resin having a melting point higher than the temperature of the solution L to be measured and lower than the temperature when heated by the electrode heater 23 described later.

An inner solution 13e with known properties is filled between the protection plate 21 and the liquid junction 13a of the second reference electrode unit 13. The "properties" of the inner solution 13e include, for example, a pH concentration. The inner solution 13e may be the same solution as the inner solution 13b, a solution having the same pH concentration as and composed of components different from the inner solution 13b, or a solution completely different from the inner solution 13b.

In this manner, since the outside of the liquid junction 13a is protected by the inner solution 13e and the protection plate 21, diffusion of the inner solution 13b to the solution L is suppressed. The inner solution 13e and the protection plate 21 suppress degradation of the internal electrode 13c, and maintain the second reference electrode unit 13 in the unused state which is the state before the second reference electrode unit 13 comes into contact with the solution L.

The protection unit 20 further has an electrode heater 23 that heats the attaching portion of the protection plate 21 to the measuring unit 10. The heat-soluble adhesive 22 described above is provided to the attaching portion of the protection plate 21 to the measuring unit 10, more specifically, the attaching portion of the protection plate 21 to the support 13d of the second reference electrode unit 13. The electrode heater 23 is disposed near the heat-soluble adhesive 22, and as illustrated in FIG. 1, is connected to the controller 40 via a conduction wire 24 as illustrated in FIG. 1. The electrode heater 23 heats the heat-soluble adhesive 22 on the basis of control by the controller 40.

Figure 4:
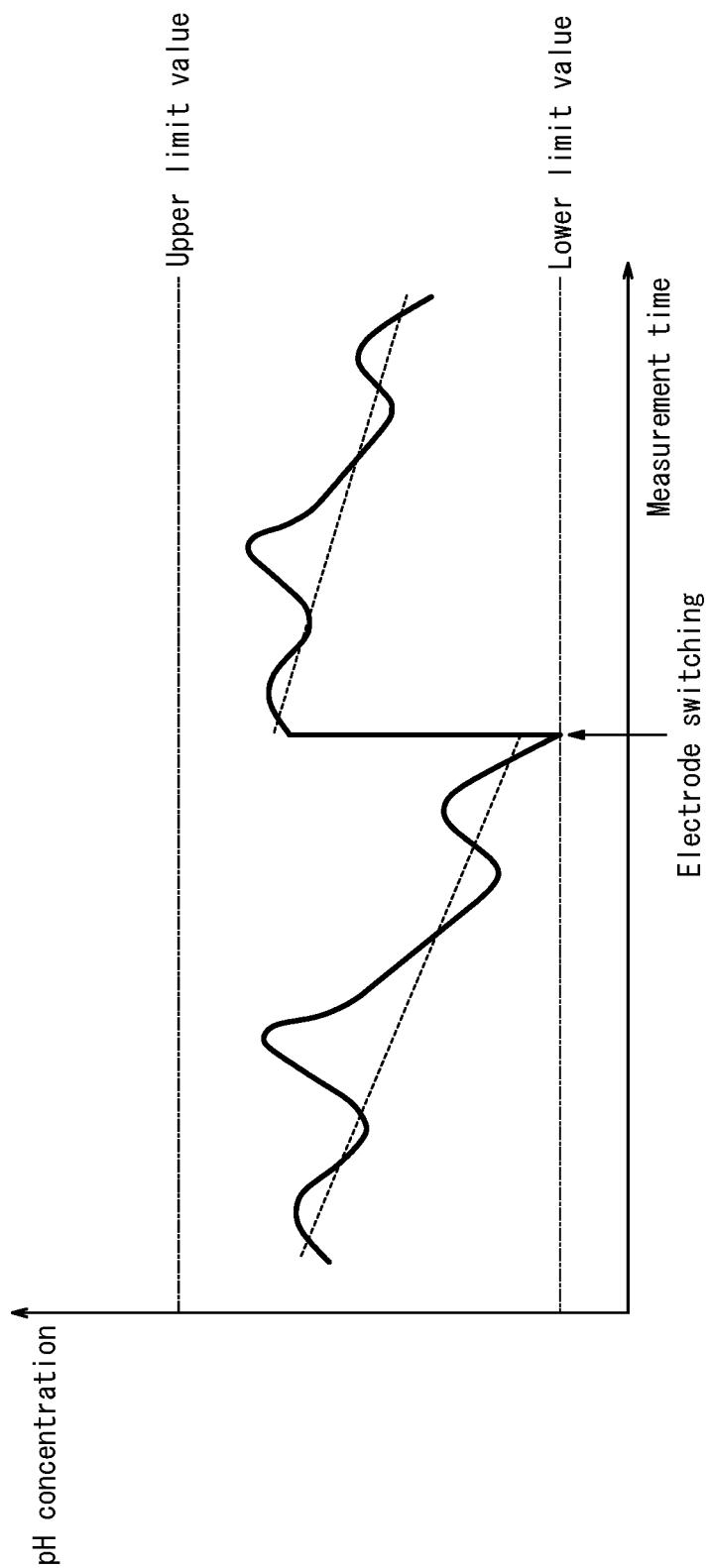
FIG. 4 is a schematic diagram illustrating time dependency of a pH concentration of the solution obtained by the measuring device in FIG. 1.

FIG. 4 is a schematic diagram illustrating time dependency of the pH concentration of the solution L obtained by the measuring device 1 in FIG. 1. The vertical axis of FIG. 4 represents the pH concentration of the solution L and the horizontal axis of FIG. 4 represents the measurement time. The dashed lines illustrated in the example of the measurement graph of FIG. 4 represent drift of the measured value of the pH concentration of the solution L.

Referring to FIG. 4, the measured value of the pH concentration of the solution L obtained by the measuring device 1 drifts in a fixed direction over the measurement time. When the actual pH concentration of the solution L changes, the measured value of the pH concentration of the solution L also changes correspondingly. However, even if the actual pH concentration of the solution L is fixed, the measured value of the pH concentration of the solution L shows a drift such that the measured value decreases at a constant rate. The user has some estimates on the pH concentration of the solution L, and the measuring device 1 is appropriately selected by the user so as to have a measurement range corresponding to the pH concentration of the solution L. That is, the measuring device 1 has a predetermined range that can be measured.

The controller 40 determines whether or not the measured value of the information on the state of the solution L exceeds a predetermined range that can be measured by the first part P1 of the measuring unit 10. For example, due to the above described drift, the measured value of the information on the state of the solution L exceeds, at a certain measurement time, the lower limit value of a predetermined range that can be measured by the measuring device 1. The measured value of the information on the state of the solution L takes a zero value or increases and goes off the scale when all of the inner solution 12b of the first reference electrode unit 12 flows to the solution L and the remaining amount of the inner solution 12b in the first reference electrode unit 12 becomes zero. At this time, the measured value of the information on the state of the solution L exceeds the lower limit value or the upper limit value in a predetermined range that can be measured by the measuring device 1. When a foreign matter attaches to the surface of the glass thin film 11a, for example, the measured value of the information on the state of the solution L exceeds the lower limit value or the upper limit value in a predetermined range that can be measured by the measuring device 1 and keeps a specific pH concentration determined by the foreign matter.

When determining that the measured value of the information on the state of the solution L exceeds a predetermined range, the controller 40 heats the electrode heater 23 to remove the protection plate 21 from the measuring unit 10 through heating by the electrode heater 23. At this time, the controller 40 obtains a measurement signal based on the second part P2. More specifically, the controller 40 switches the measurement using the glass electrode unit 11 and the first reference electrode unit 12 to the measurement using the glass electrode unit 11 and the second reference electrode unit 13. In response to such a switching of measurement by the controller 40, the voltage detector 30 switches the connection to the internal electrode 12c of the first reference electrode unit 12 to the connection to the internal electrode 13c of the second reference electrode unit 13.

Figure 5:
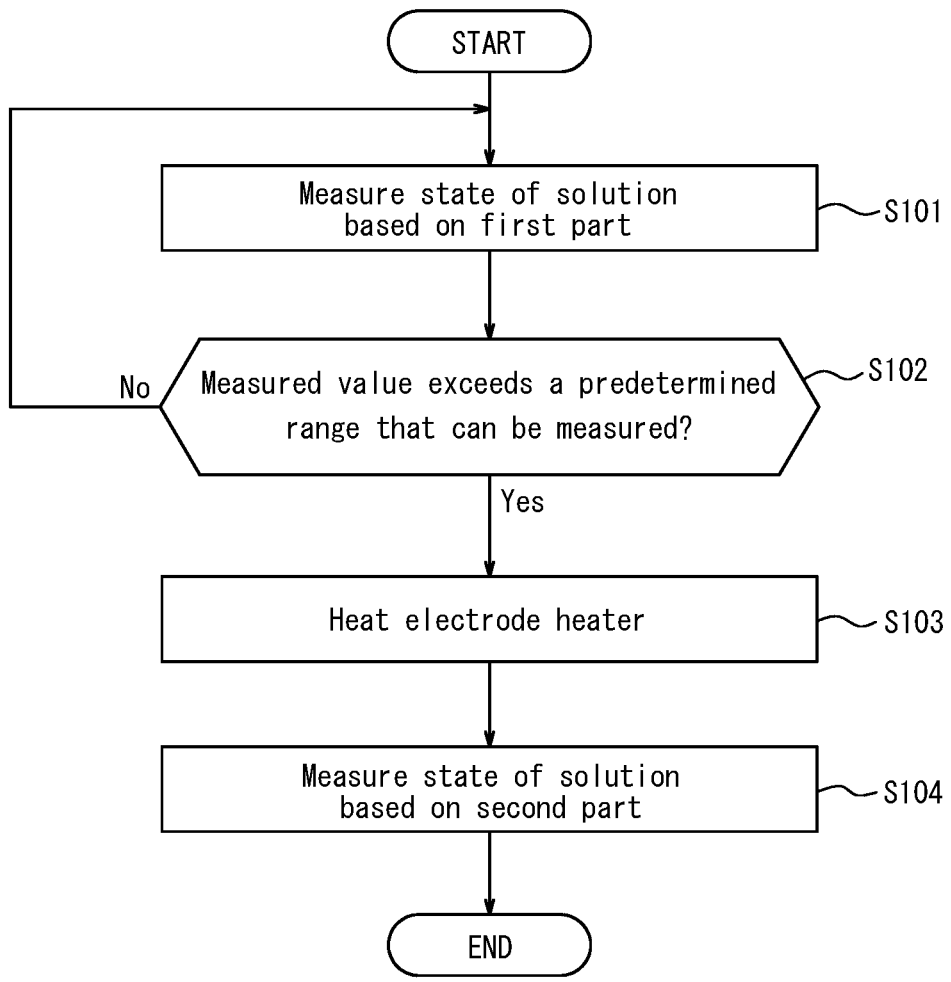
FIG. 5 is a flowchart illustrating an example of operation of the measuring device in FIG. 1.

FIG. 5 is a flowchart illustrating an example of operation of the measuring device 1 in FIG. 1. An example of operation of the measuring device 1 will be mainly described with reference to FIG. 5.

In step S101, the measuring device 1 measures the state of the solution L based on the first part P1. More specifically, the controller 40 continuously obtains the information on the state of the solution L based on the voltage signal output from the measuring unit 10 using the glass electrode unit 11 and the first reference electrode unit 12.

In step S102, the controller 40 determines whether or not the measured value of the information on the state of the solution L exceeds a predetermined range that can be measured by the first part P1 of the measuring unit 10. If the controller 40 determines that the measured value of the information on the state of the solution L exceeds the predetermined range, the process proceeds to step S103. If the controller 40 determines that the measured value of the information on the state of the solution L does not exceed the predetermined range, the process goes back to step S101.

In step S103, the controller 40 stops measurement based on the first reference electrode unit 12, heats the electrode heater 23 and detaches the protection plate 21 from the measuring unit 10 through heating by the electrode heater 23. More specifically, the controller 40 melts the heat-soluble adhesive 22 that bonds the protection plate 21 to the support 13d by the electrode heater 23 to detach the protection plate 21. When the protection plate 21 is composed of acid-soluble resin and the solution L is acidic, the thickness of the protection plate 21 may be determined by the measurement time when the measured value of the pH concentration of the solution L exceeds the lower limit value due to drift and the acid concentration of the solution L. More specifically, the thickness of the protection plate 21 is such that the protection plate 21 is not completely dissolved by the solution L before the measured value of pH concentration of the solution L exceeds the lower limit value due to drift. The detached protection plate 21 is dissolved by the solution L and disappears.

In step S104, the measuring device 1 measures the state of the solution L based on the second part P2. More specifically, the controller 40 continuously obtains the information on the state of the solution L based on the voltage signal output from the measuring unit 10 using the glass electrode unit 11 and the second reference electrode unit 13.

According to the measuring device 1 of the first embodiment as described above, the state of the solution L can be measured over a long period of time, and the user convenience is improved. More specifically, the measuring unit 10 has, in addition to the first part P1, the second part P2 in the standby state for measurement. Thus, while the measuring device 1 is kept small, the cycle of maintenance work including calibration and refill of the inner solution 12b is extended, enabling a long-term measurement. Even if the measurement based on the first reference electrode unit 12 becomes impossible, the measurement can be continued based on the second reference electrode unit 13. This allows for a long-term measurement with the measuring device 1 introduced into a biological body or a process from which the measuring device 1 is difficult to be removed. For example, when the measuring device 1 is used, a continuous measurement on a year-to-year basis is possible.

The information on the state of the solution L is transmitted to any external device by the communication unit 50, thus the user can obtain the information on the state of the solution L even if the user is not at the site where the measuring device 1 is installed, for example, by using a communication method such as wireless communication.

Variations of the measuring device 1 according to the first embodiment will be mainly described below with reference to FIGS. 6-8.

Figure 6:
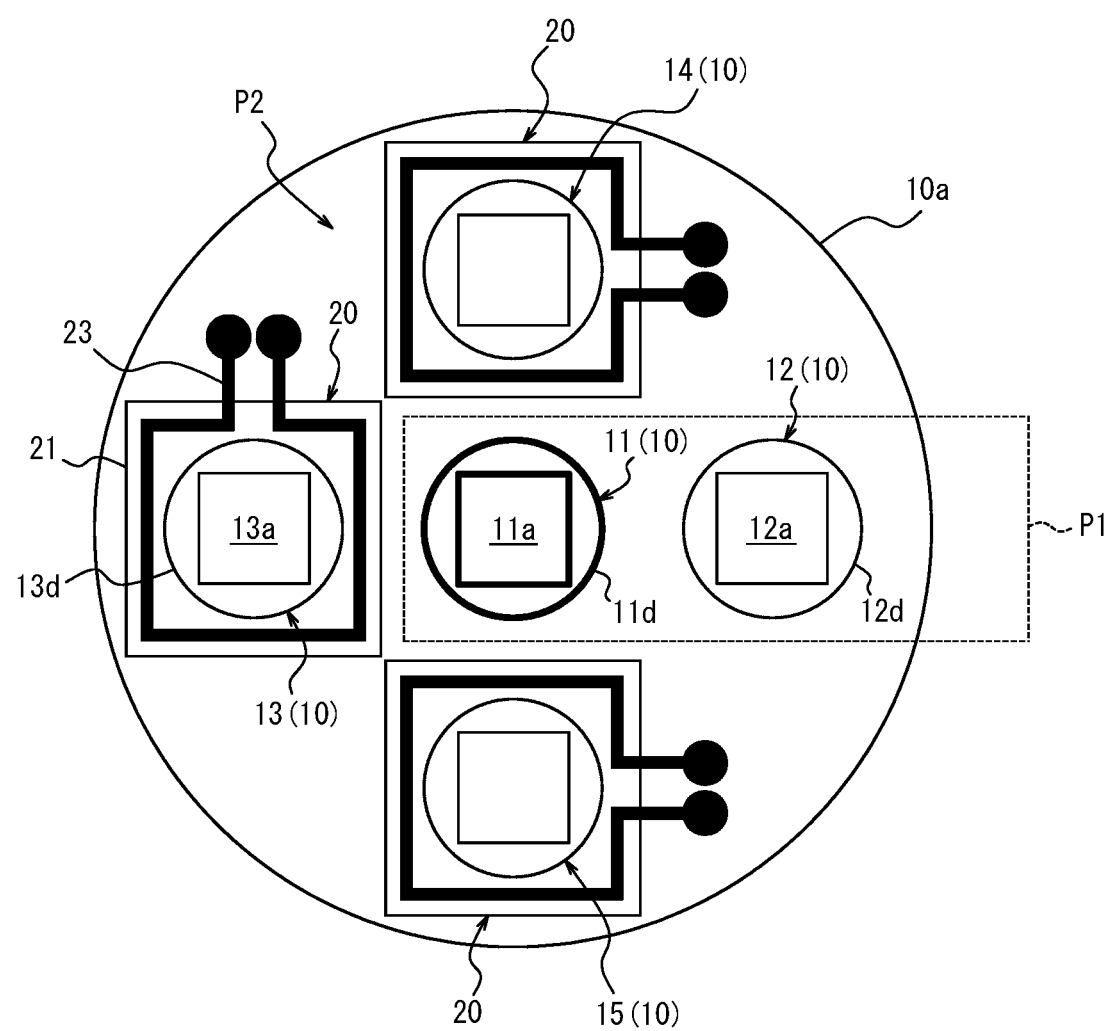
FIG. 6 is a schematic diagram illustrating a first variation of the measuring device in FIG. 1.

FIG. 6 is a schematic diagram illustrating a first variation of the measuring device 1 in FIG. 1. FIG. 6 illustrates the measuring unit 10 and the protection unit 20 of the measuring device 1 viewed from the bottom.

In the first embodiment, the measuring unit 10 is described as having one glass electrode unit 11 and two reference electrode units, but is not limited thereto. The measuring unit 10 may have three or more reference electrode units for one glass electrode unit 11. Referring to FIG. 6, the measuring unit 10 may further include a third reference electrode unit 14 and a fourth reference electrode unit 15, for example, in addition to the glass electrode unit 11, the first reference electrode unit 12 and the second reference electrode unit 13.

In this case, the protection unit 20 similar to one that attached to the second reference electrode unit 13 may be attached also to the third reference electrode unit 14 and the fourth reference electrode unit 15. That is, the first part P1 of the measuring unit 10 in the usable state has a pair of the glass electrode unit 11 and the first reference electrode unit 12, which is the same as above. The second part P2 of the measuring unit 10 in the standby state for measurement further has, in addition to the second reference electrode unit 13, the third reference electrode unit 14 and the fourth reference electrode unit 15.

The distance between the internal electrode 11c contained in the glass electrode unit 11 and the internal electrode contained in each reference electrode unit may be the same. For example, the internal electrodes each contained in reference electrode units may be disposed concentrically with the internal electrode 11c contained in the glass electrode unit 11 as the center. This reduces the measurement error between the measurement results when using the internal electrode 11c and the internal electrode of each reference electrode unit because the distance between the internal electrode 11c of the glass electrode unit 11 and the internal electrode of each reference electrode unit is constant.

In the above embodiment, the protection plate 21 is described as being attached to the end surface side of the corresponding support through the heat-soluble adhesive 22, but the attachment method of the protection plate 21 is not limited thereto. The protection plate 21 may be fixed by any method. For example, when it is necessary to fix a plurality of protection plates 21 as illustrated in FIG. 6, instead of attaching to each corresponding support, a plurality of protection plates 21 may be attached to the end surface side of the support 10a that collectively contains each electrode unit through the heat-soluble adhesive 22.

The protection plate 21 may be directly attached to the end surface of the corresponding support without using the heat-soluble adhesive 22, instead of being attached to the end surface side of the corresponding support through the heat-soluble adhesive 22. That is, the heat-soluble adhesive 22 is not necessary. At this time, the protection plate 21 is composed of any resin having a melting point higher than the temperature of the solution L to be measured and lower than the temperature when heated by the electrode heater 23. In this manner, the protection plate 21 can be properly detached at a predetermined measurement time through control of the electrode heater 23 by the controller 40.

Figure 7:
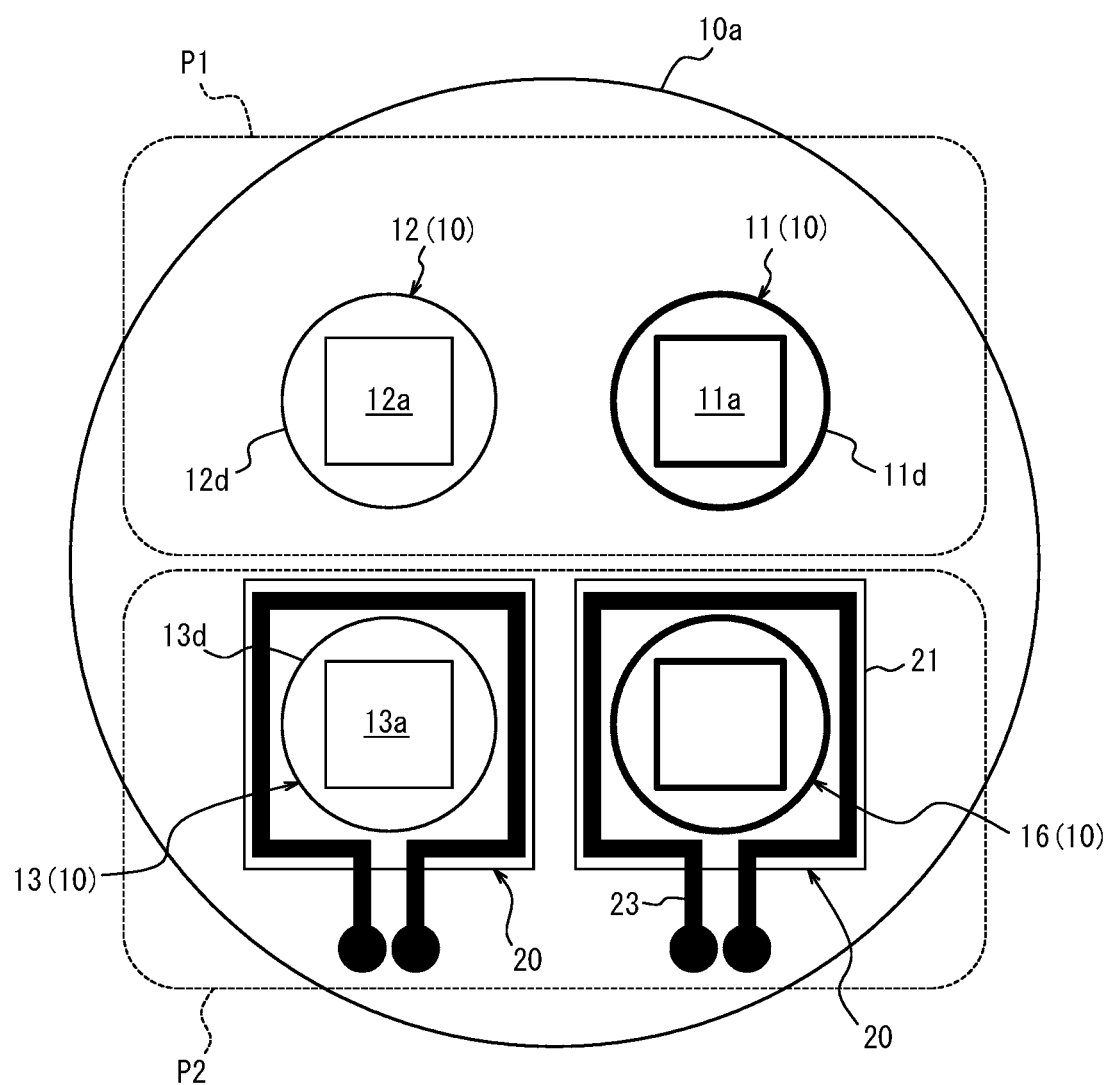
FIG. 7 is a schematic diagram illustrating a second variation of the measuring device in FIG. 1.

FIG. 7 is a schematic diagram illustrating a second variation of the measuring device 1 in FIG. 1. FIG. 7 illustrates the measuring unit 10 and the protection unit 20 of the measuring device 1 viewed from the bottom.

In the above, the measuring unit 10 is described as having one glass electrode unit 11, but is not limited thereto. The measuring unit 10 may have two or more glass electrode units. For example, as illustrated in FIG. 7, the measuring unit 10 may have another pair of a glass electrode unit 16 and a second reference electrode unit 13, in addition to a pair of the glass electrode unit 11 and the first reference electrode unit 12. At this time, the protection unit 20, which is the same as the above described protection unit 20 attached to the second reference electrode unit 13, may be attached to the glass electrode unit 16. That is, the first part P1 of the measuring unit 10 in the usable state has a pair of the glass electrode unit 11 and the first reference electrode unit 12, which is the same as above. The second part P2 of the measuring unit 10 in the standby state for measurement has a pair of the glass electrode unit 16 and the second reference electrode unit 13. From mentioned above, the protection plate 21 suppresses deterioration of the glass electrode unit 16 in addition to the second reference electrode unit 13. For example, it is possible to suppress adhesion of foreign matter to the surface of the glass thin film of the glass electrode unit 16, and to suppress contamination of the glass thin film.

The distance between the internal electrode 11c contained in the glass electrode unit 11 and the internal electrode 12c contained in the first reference electrode unit 12 may be the same as the distance between the internal electrode contained in the glass electrode unit 16 and the internal electrode 13c contained in the second reference electrode unit 13. Thus, the distance between each internal electrode of a pair of a glass electrode unit and a reference electrode unit is the same as that of a different pair. Therefore, the measurement error is reduced between measurement results when each pair of the internal electrode of the glass electrode units and the internal electrode of the reference electrode unit is used.

Figure 8:
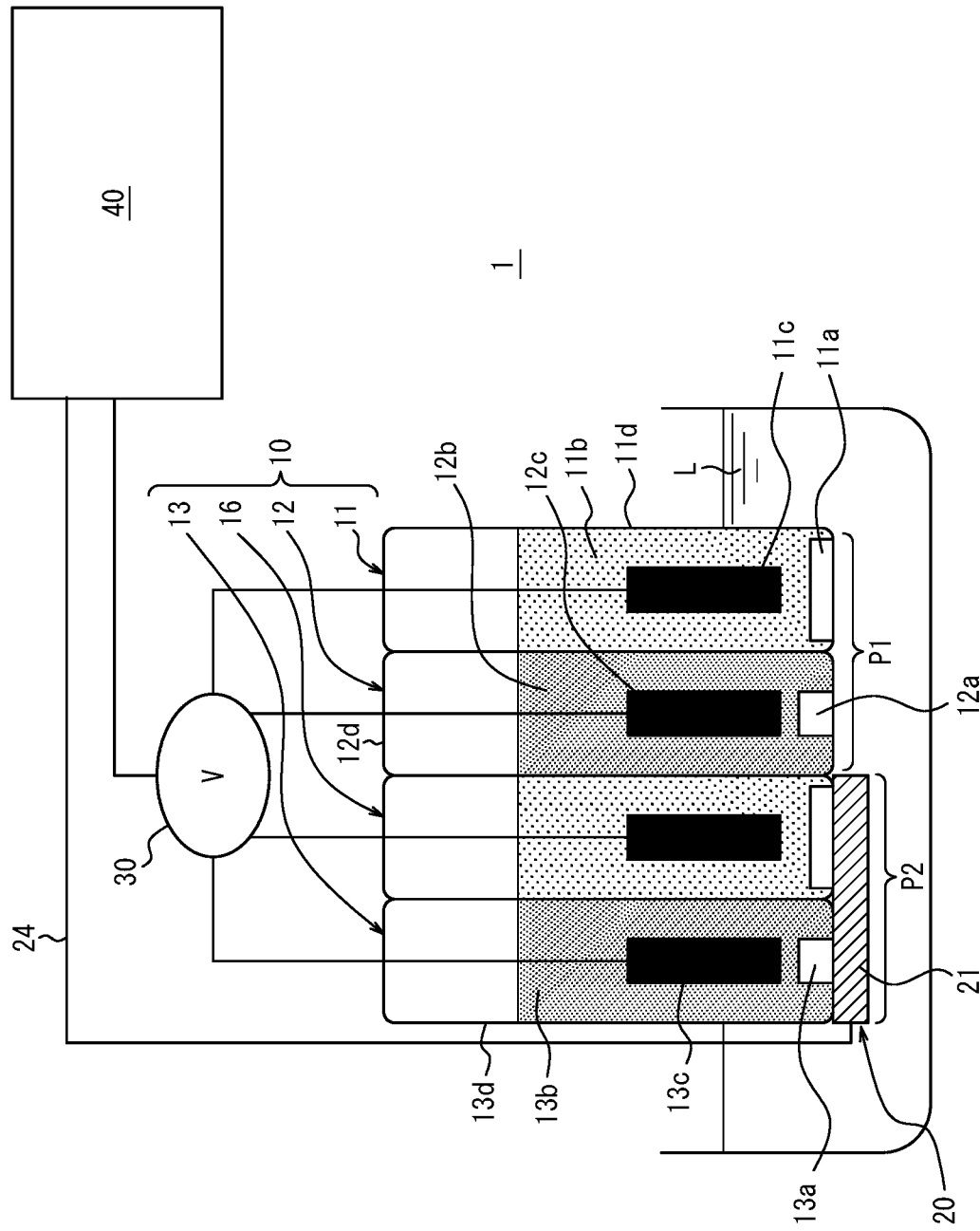
FIG. 8 is a schematic diagram illustrating a third variation of the measuring device in FIG. 1.

FIG. 8 is a schematic diagram illustrating a third variation of the measuring device 1 in FIG. 1.

In the above, the protection plate 21 is described as being individually attached to each electrode unit contained in the second part P2 of the measuring unit 10, but the attachment method of the protection plate 21 is not limited thereto. For example, as illustrated in FIG. 8, as with FIG. 7, when the second part P2 of the measuring unit 10 in the standby state for measurement has a pair of the glass electrode unit 16 and the second reference electrode unit 13, the protection plate 21 may be attached collectively to the pair of the glass electrode unit 16 and the second reference electrode unit 13.

As illustrated in FIGS. 7 and 8, even when a pair of the glass electrode unit 16 and the second reference electrode unit 13 are contained in the second part P2 of the measuring unit 10, an inner solution 13e with known properties may be filled between the protection plate 21 and the second part P2 of the measuring unit 10. This allows for calibration using the glass electrode unit 16 and the second reference electrode unit 13 until immediately before the controller 40 detaches the protection plate 21. More specifically, before the protection plate 21 is detached, the measuring device 1 measures the inner solution 13e with known pH concentration using the glass electrode unit 16 and the second reference electrode unit 13. In this manner, the controller 40 and the user can determine whether the known pH concentration and the measured value are the same or not. This allows for easy calibration of the measuring device 1.

In the above, the inner solution 13e is described as being any solution, but is not limited thereto. The inner solution 13e may be any gel.

In the above description, measurement is switched when the controller 40 determines whether or not the measured value of the information on the state of the solution L exceeds the predetermined range that can be measured by first part P1 of measuring unit 10. However, the determination method is not limited thereto. For example, the controller 40 may calculate the measurement life T in advance on the basis of the slope of the drift calculated by calibration before starting to use the measuring device 1 and the lower limit value of the predetermined range that can be measured. For example, the controller 40 may calculate the measurement life T in advance on the basis of the initial filling amount of the inner solution 12b of the first reference electrode unit 12 and the amount of the inner solution 12b flowing out from the liquid junction 12a per unit time.

The controller 40 may store the calculated measurement life T in a memory 60 and compare the operating time of the first part P1 of the measuring unit 10 with the measurement life T calculated in advance. For example, when determining that the measurement life T is not reached, the controller 40 continues measurement based on the first part P1 of the measuring unit 10. For example, when determining that the measurement life T is reached, the controller 40 switches to the measurement based on the second part P2 of the measuring unit 10.

For example, the controller 40 may measure the remaining amount of the inner solution 12b based on any sensor installed inside the support 12d in real time to determine whether or not the remaining amount of the inner solution 12b becomes zero. For example, when determining that the remaining amount of the inner solution 12b is not zero, the controller 40 continues measurement based on the first part P1 of the measuring unit 10. For example, when determining that the remaining amount of the inner solution 12b is zero, the controller 40 switches to the measurement based on the second part P2 of the measuring unit 10.

In the above description, the protection plate 21 is detached by controlling the electrode heater 23. However, the removal method of the protection plate 21 is not limited thereto. For example, the protection unit 20 may not have the electrode heater 23. In this case, the protection plate 21 is composed of, for example, biodegradable resin or acid-soluble resin, and is gradually decomposed or dissolved by the solution L. The protection plate 21 is formed to have a thickness such that the time during which the protection plate 21 is completely decomposed or dissolved and the measurement life T are substantially the same. The electrode heater 23 is not needed any more with the above described configuration. Thus consumption of a battery attached as a power source to the measuring device 1 is suppressed. Since the space for attaching the electrode heater 23 is saved, the measuring device 1 is downsized.

The measuring device 1 may further have a temperature sensor that is installed at any position such as an exterior wall of each support, for example, and measures the temperature of the solution L. This allows the controller 40 to correct the measured value of the information on the state of the solution L on the basis of the measured temperature of the solution L. Such a temperature sensor may be disposed between the protection plate 21 and the second part P2. This isolates the temperature sensor from the solution L during measurement based on the first part P1. Therefore, degradation of the temperature sensor is suppressed, and when the measurement based on the second part P2 is started, the temperature sensor can detect, in an unused state, the temperature.

Second Embodiment

Figure 9:
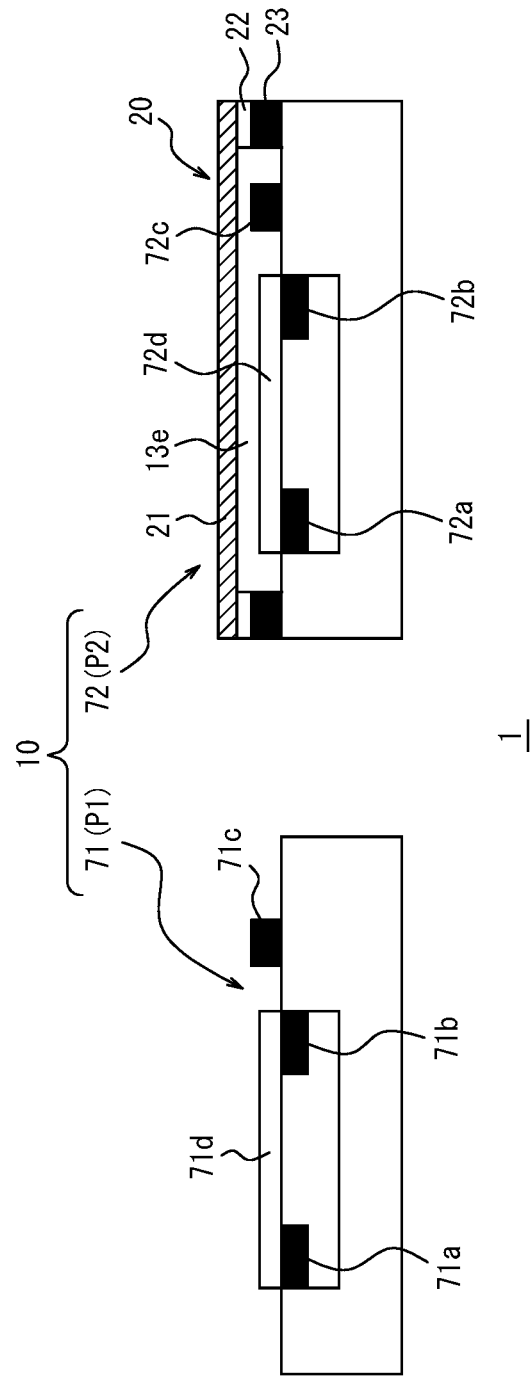
FIG. 9 is a schematic diagram illustrating an example of configuration of a measuring device according to a second embodiment.

FIG. 9 is a schematic diagram illustrating an example of configuration of the measuring device 1 according to a second embodiment. Configuration and function of the measuring device 1 according to the second embodiment will be mainly described with reference to FIG. 9.

In the description of the first embodiment, the information on the state of the solution L includes a pH concentration, and the measuring unit 10 has each electrode unit used for the glass electrode type pH measurement, but not limited thereto. In the measuring device 1 according to the second embodiment, for example, the information on the state of the solution L includes ion concentration, and the measuring unit 10 may have a first ISFET 71 and a second ISFET 72. The configuration of the measuring device 1 according to the second embodiment is the same as that of the first embodiment other than the measuring unit 10, and the above description for the first embodiment is applied as it is to the second embodiment. The same reference signs are given to the same configurations as those in the first embodiment, and the description thereof will be omitted. The points different from the first embodiment will be mainly described.

Referring to FIG. 9, the measuring unit 10 has a first ISFET 71 and a second ISFET 72. The first ISFET 71 has a measurement electrode including a source electrode 71a and a drain electrode 71b and a reference electrode 71c. The first ISFET 71 has an ion sensitive film 71d disposed over the source electrode 71a and the drain electrode 71b. Similarly, the second ISFET 72 has a measurement electrode including a source electrode 72a and a drain electrode 72b and a reference electrode 72c. The second ISFET 72 has an ion sensitive film 72d disposed over the source electrode 72a and the drain electrode 72b.

The first part P1 of the measuring unit 10 has the first ISFET 71. The second part P2 of the measuring unit 10 has the second ISFET 72. The protection unit 20 is not attached to the first ISFET 71, and the ion sensitive film 71d of the first ISFET 71 is in contact with the solution L. On the other hand, the protection unit 20 is attached to the second ISFET 72, and an ion sensitive film 72d of the second ISFET 72 is isolated from the solution L. Therefore, the protection unit 20 suppresses deterioration including adhesion of foreign matters, alteration, scraping and the like in the ion sensitive film 72d of the second ISFET 72.

The measuring unit 10 of the measuring device 1 according to the second embodiment may further have some ISFETs having the same configuration as the second ISFET 72 to which the protection unit 20 is attached.

The measuring device 1 according to the second embodiment as described above has the same effect as that of the first embodiment. In the measuring device 1 according to the second embodiment, the measuring unit 10 is composed of a small ISFET. Therefore, even if the number of components of the second part P2 is increased as compared with that of the first embodiment, the measuring device 1 is kept small. The measuring device 1 according to the second embodiment can extend the maintenance work cycle even when it is kept small, and allows for a long-term measurement.

Third Embodiment

Figure 10:
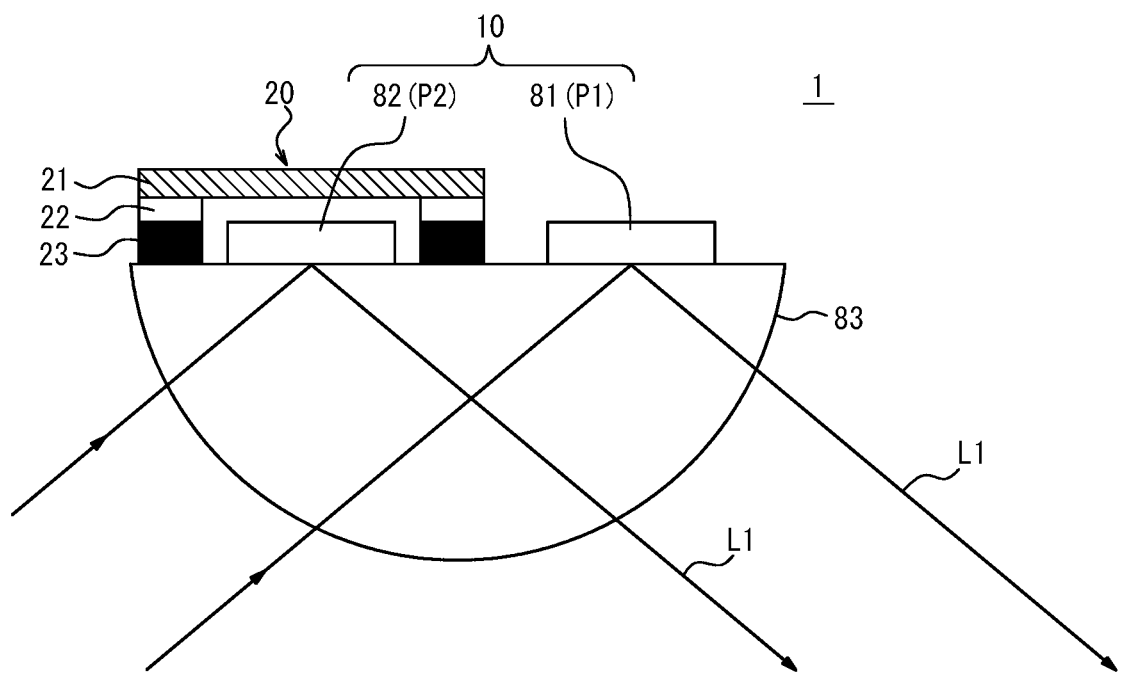
FIG. 10 is a schematic diagram illustrating an example of configuration of a measuring device according to a third embodiment.

FIG. 10 is a schematic diagram illustrating an example of configuration of the measuring device 1 according to a third embodiment. Configuration and function of the measuring device 1 according to the third embodiment will be mainly described with reference to FIG. 10.

In the measuring device 1 according to the third embodiment, the information on the state of the solution L includes the ion concentration or the amount of chemical component composition, for example, and the measuring unit 10 may have a first metal thin film 81, a second metal thin film 82, a prism substrate 83 and a photo detector not illustrated. The configuration of the measuring device 1 according to the third embodiment is the same as that of the first embodiment other than the measuring unit 10, and the above description for the first embodiment is applied as it is to the configuration of the third embodiment. The same reference signs are given to the same configurations as those in the first embodiment, and the description thereof will be omitted. The points different from the first embodiment will be mainly described.

The measuring unit 10 has the first metal thin film 81, the second metal thin film 82, the prism substrate 83 and a photo detector not illustrated. The first metal thin film 81 or the second metal thin film 82 is irradiated with a measurement light L1 via the prism substrate 83. For example, the controller 40 obtains the light absorption spectrum of the solution L that is in contact with the first metal thin film 81 by detecting the measurement light L1 reflected on the surface of the first metal thin film 81 with a photo detector. The controller 40 analyzes the ion concentration or the chemical composition amount of each component in the solution L on the basis of the obtained light absorption spectrum.

The first part P1 of the measuring unit 10 has the first metal thin film 81. The second part P2 of the measuring unit 10 has the second metal thin film 82. The protection unit 20 is not attached to the first metal thin film 81, and the first metal thin film 81 is in contact with the solution L. On the other hand, the protection unit 20 is attached to the second metal thin film 82, and the second metal thin film 82 is isolated from the solution L. Therefore, in the second metal thin film 82, the protection unit 20 suppresses deterioration including adhesion of foreign matters, alteration, scraping and the like.

The measuring unit 10 of the measuring device 1 according to the third embodiment may further have some metal thin films having the same configuration as that of the second metal thin film 82 to which the protection unit 20 is attached.

The measuring device 1 according to the third embodiment described above produces the same effect as that produced by the first embodiment. In the measuring device 1 according to the third embodiment, unlike the first embodiment and the second embodiment, there is no drift of the measurement signal. Therefore, the measuring device 1 can measure the state of the solution L over a long period of time as long as the metal thin film is not deteriorated due to factors including adhesion of foreign matters, alteration, scraping and the like. Even if the metal thin film deteriorates, the measuring unit 10 of the measuring device 1 has the second part P2, thus the measuring device 1 can extend the maintenance work cycle and allows for a long-term measurement.

It is obvious to those skilled in the art that the present disclosure can be realized in predetermined forms other than the embodiments described above, without departing from its spirit or its essential features. Therefore, the above description is exemplary and is not limited thereto. The scope of disclosure is defined by the appended claims, not by the foregoing description. All changes which come within the range of equivalency of the claims are intended to be embraced therein.

For example, the shape, the disposition, the orientation, the number, and the like of each component described above are not limited to the contents illustrated in the above description and drawings. The shape, the disposition, the orientation, the number, and the like of each component may have any configuration as long as the function thereof can be realized.

For example, functions and the like included in the above described each step of the measuring method using the measuring device 1 can be rearranged without logical inconsistency, and a plurality of steps can be combined into one or divided.

REFERENCE SIGNS LIST

1 Measuring device
10 Measuring unit
10a Support
11 Glass electrode unit
11a Glass thin film
11b Inner solution
11c Internal electrode
11d Support
12 First reference electrode unit
12a Liquid junction 12b Inner solution
12c Internal electrode
12d Support
13 Second reference electrode unit
13a Liquid junction
13b Inner solution
13c Internal electrode
13d Support
13e Inner solution
14 Third reference electrode unit
15 Fourth reference electrode unit
16 Glass electrode unit
20 Protection unit
21 Protection plate
22 Heat-soluble adhesive
23 Electrode heater
24 Conduction wire
30 Voltage detector
40 Controller
50 Communication unit
60 Memory
71 First ISFET
71a Source electrode
71b Drain electrode
71c Reference electrode
71d Ion sensitive film
72 Second ISFET
72a Source electrode
72b Drain electrode
72c Reference electrode
72d Ion sensitive film
81 First metal thin film
82 Second metal thin film
83 Prism substrate
L Solution
L1 Measurement light
P1 First part
P2 Second part
T Measurement life

The invention claimed is:

1. A measuring device configured to measure a state of a solution, comprising:
   a measuring unit configured to output a measurement signal associated with the state of the solution;
   a protection unit attached to the measuring unit; and
   a controller configured to obtain information on the state of the solution on the basis of the measurement signal output from the measuring unit, wherein
   the measuring unit has:
   a first part in a usable state that contributes to output of the measurement signal by coming into contact with the solution; and
   a second part that is isolated from the solution by the protection unit and is in a standby state for measurement, and wherein
   the information on the state of the solution includes a pH concentration;
   the measuring unit has a glass electrode unit, a first reference electrode unit and a second reference electrode unit configured for glass electrode pH measurement;
   the first part has the glass electrode unit and the first reference electrode unit paired together;
   the second part has the second reference electrode unit;
   the protection unit has a protection plate configured to isolate the second part of the measuring unit from the solution; and
   the protection plate is composed of at least one of biodegradable resin and acid-soluble resin.

2. The measuring device according to claim 1, wherein the protection unit further has a heater configured to heat an attaching portion of the protection plate to the measuring unit.

3. The measuring device according to claim 2, wherein the attaching portion includes a thermally soluble adhesive having a melting point higher than a temperature of the solution and lower than a temperature when heated by the heater; and the protection plate is attached to the measuring unit by adhesion with the thermally soluble adhesive.

4. The measuring device according to claim 2, wherein the controller is configured to detach the protection plate from the measuring unit through heating by the heater when determining that a measured value of the information on the state of the solution exceeds a predetermined range that can be measured by the first part of the measuring unit, and to obtain the measurement signal based on the second part.

5. The measuring device according to claim 1, wherein an inner solution or gel with known properties is filled between the protection plate and the second part of the measuring unit.

6. The measuring device according to claim 1, wherein a distance between an internal electrode contained in the glass electrode unit and an internal electrode contained in the first reference electrode unit is the same as a distance between the internal electrode contained in the glass electrode unit and an internal electrode contained in the second reference electrode unit.

* * * * *